United States Patent [19]

Jarman

[11] 4,324,763
[45] Apr. 13, 1982

[54] INCENSE BURNING APPARATUS

[76] Inventor: James C. Jarman, 3610 Gramby St., Landover, Md. 20784

[21] Appl. No.: 256,826

[22] Filed: Apr. 23, 1981

[51] Int. Cl.³ .............................................. A61L 9/03
[52] U.S. Cl. ..................................... 422/116; 43/125;
43/144; 422/126; 422/166; 431/73; 431/86;
431/87; 431/289; 431/295
[58] Field of Search ............... 422/116, 126, 165, 166,
422/4; 431/289, 295, 28, 67, 73, 87, 86; 43/125,
127, 129, 144

[56] References Cited

U.S. PATENT DOCUMENTS

| | | | |
|---|---|---|---|
| 1,089,199 | 3/1914 | Fitzpatrick | 431/87 |
| 1,948,635 | 2/1934 | Sykes | 422/126 X |
| 2,127,975 | 8/1938 | Kemp et al. | 422/126 |
| 2,499,118 | 2/1950 | Sipes | 431/87 X |
| 2,686,944 | 8/1954 | Gubelin | 422/116 X |
| 2,793,516 | 5/1957 | McDermott | 431/295 X |
| 2,818,714 | 1/1958 | Inns | 431/295 X |
| 2,905,049 | 9/1959 | Lanbe | 422/4 X |
| 3,436,191 | 4/1969 | McGoff et al. | 422/120 X |
| 3,482,568 | 12/1969 | Bovard | 422/120 X |
| 4,155,979 | 5/1979 | Powell | 422/126 |
| 4,209,491 | 6/1980 | Rich | 422/166 X |

FOREIGN PATENT DOCUMENTS 601295 5/1948 United Kingdom ................ 422/166

Primary Examiner—Barry Richman

[57] ABSTRACT

In an apparatus for successively igniting a plurality of incense sticks or other elongated combustible articles, a series of timer discs on a common shaft is rotated by an electric motor. The rim of each disc is provided with a bore for holding one end of an incense stick. The opposite end of the stick is supported beneath an igniter element. As the motor shaft rotates, the timer discs are successively rotated to move the incense sticks, one at a time, into contact with the igniter element. Following ignition, each incense stick is further rotated for exposure to the atmosphere until fully consumed. The speed of rotation of the timer discs is controlled to provide complete consumption of an incense stick during each shaft revolution.

17 Claims, 10 Drawing Figures

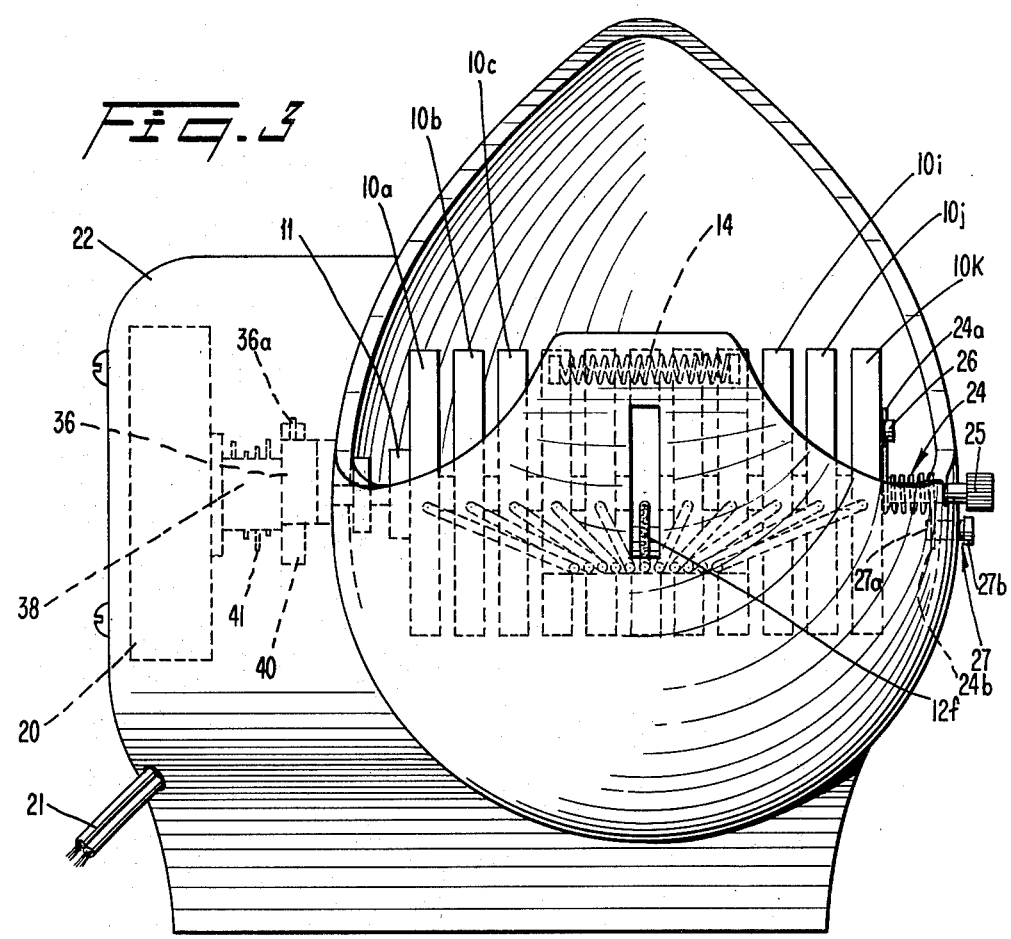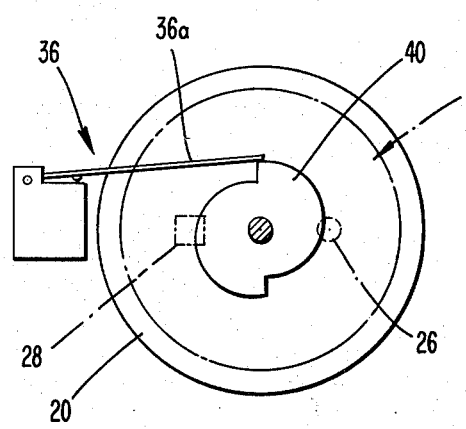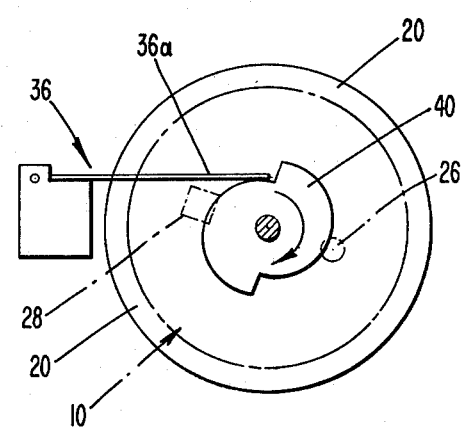

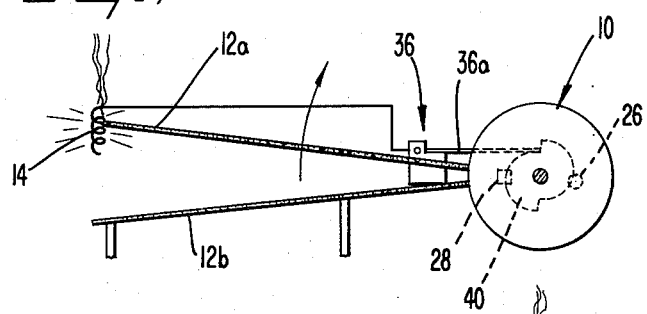
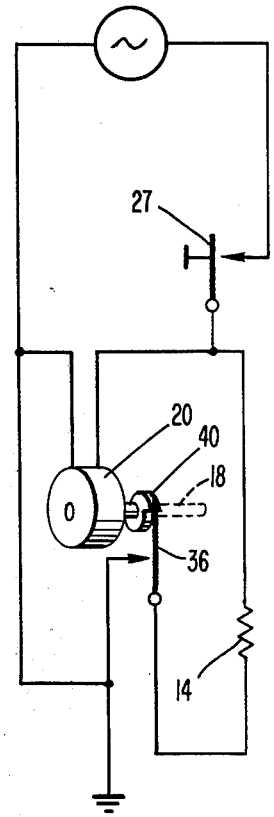
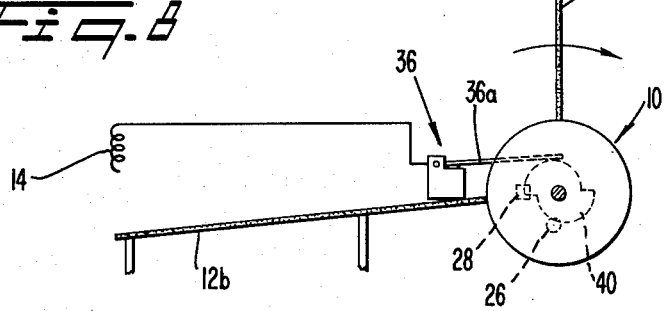
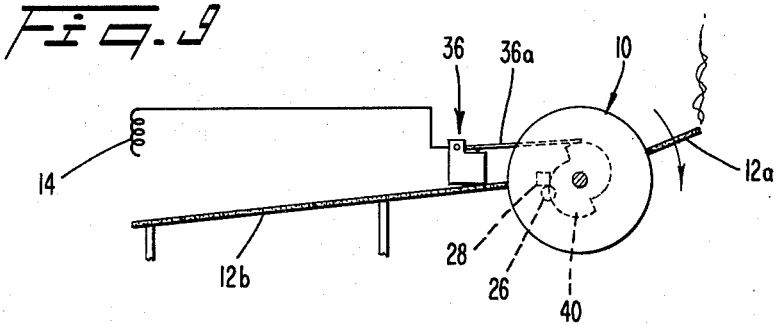
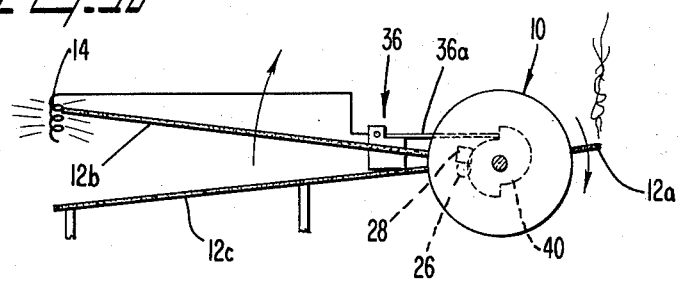

INCENSE BURNING APPARATUS

TECHNICAL FIELD

The present invention relates generally to an apparatus for providing controlled ignition and burning of elongated combustible articles and more particularly toward an incense burner for automatically successively igniting, in timed relationship, a plurality of incense sticks.

BACKGROUND ART

Various types of incense burners have been provided in the prior art wherein a single incense stick is manually ignited and supported to dispense the aroma developed by the stick to the atmosphere. Differences among various types of incense burners are substantially ornamental in nature and each type is arranged to burn only one incense stick at a time. This presents an annoying inconvenience if it is desirous to produce the fragrance of burning incense throughout an extended period of time, e.g., an entire evening, since the user must replace and ignite a fresh incense stick each time a stick is consumed. This is a problem since the user must be available throughout the evening to refill the incense burner with new sticks. There is also some risk of injury to the user since each incense stick must be manually ignited by hand using a match, lighter, or other ignition device.

Accordingly, one object of the present invention is to provide an apparatus for successively igniting a plurality of incense sticks or similar combustible articles.

Another object is to provide an apparatus for igniting a plurality of incense sticks in succession and exposing each stick to the atmosphere following ignition.

Another object is to provide an apparatus for automatically igniting a plurality of incense sticks without intervention by the user.

Another object is to provide a highly safe and reliable incense burner wherein a plurality of incense sticks are ignited in succession without user intervention and there is no risk of injury by burning.

DISCLOSURE OF INVENTION

A device for successively igniting a plurality of incense sticks, in accordance with the invention, comprises a means for supporting a supply of the sticks beneath an igniter member and successively rotating the sticks into contact with the igniter. An electric switch is synchronized to rotation of the incense sticks whereby the igniter is energized during contact with each stick for ignition. Following ignition, the burning stick is further rotated for exposure to the atmosphere.

In accordance with another aspect of the invention, the means for rotating the incense sticks comprises a series of timer discs, one for each incense stick, positioned on a common shaft that is rotated by an electric motor. The periphery of each of the discs is formed with a bore into which one end of an incense stick is supported. The opposite end of each incense stick is positioned on a support that locates the stick beneath the igniter element. The timer discs are coupled together such that the discs rotate in succession to move the incense sticks, one by one, into contact with the igniter element. A cam secured on the rotating shaft closes the electric switch during each revolution of the shaft to energize the igniter element at the appropriate time as an incense stick is brought into contact with the igniter.

The timer discs are detachable from the rotary shaft so that any number of discs can be provided depending upon the number of incense sticks to be burned.

Still other objects and advantages of the present invention will become readily apparent to those skilled in this art from the following detailed description, wherein I have shown and described only the preferred embodiment of the invention, simply by way of illustration of the best mode contemplated by me of carrying out my invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

FIG. 3 is a front view of the apparatus shown in FIG. 1;

FIG. 4 is an end view of the switch synchronizing cam, wherein the switch is open;

FIG. 5 is an end view of the switch synchronizing cam with the switch in a closed position;

FIG. 6 is a schematic diagram showing the igniter element energizing circuit;

FIG. 7 illustrates a first incense stick undergoing ignition by the igniter element;

FIG. 8 illustrates the first incense stick as it rotates beyond the igniter element for exposure to the atmosphere;

FIG. 9 shows the first incense stick as it completes a cycle of revolution just prior to rotation of a second incense stick; and FIG. 10 illustrates the second incense stick as it is moved into contact with the igniter element, with the first incense stick substantially consumed.

BEST MODE FOR CARRYING OUT THE INVENTION

Figure 1:
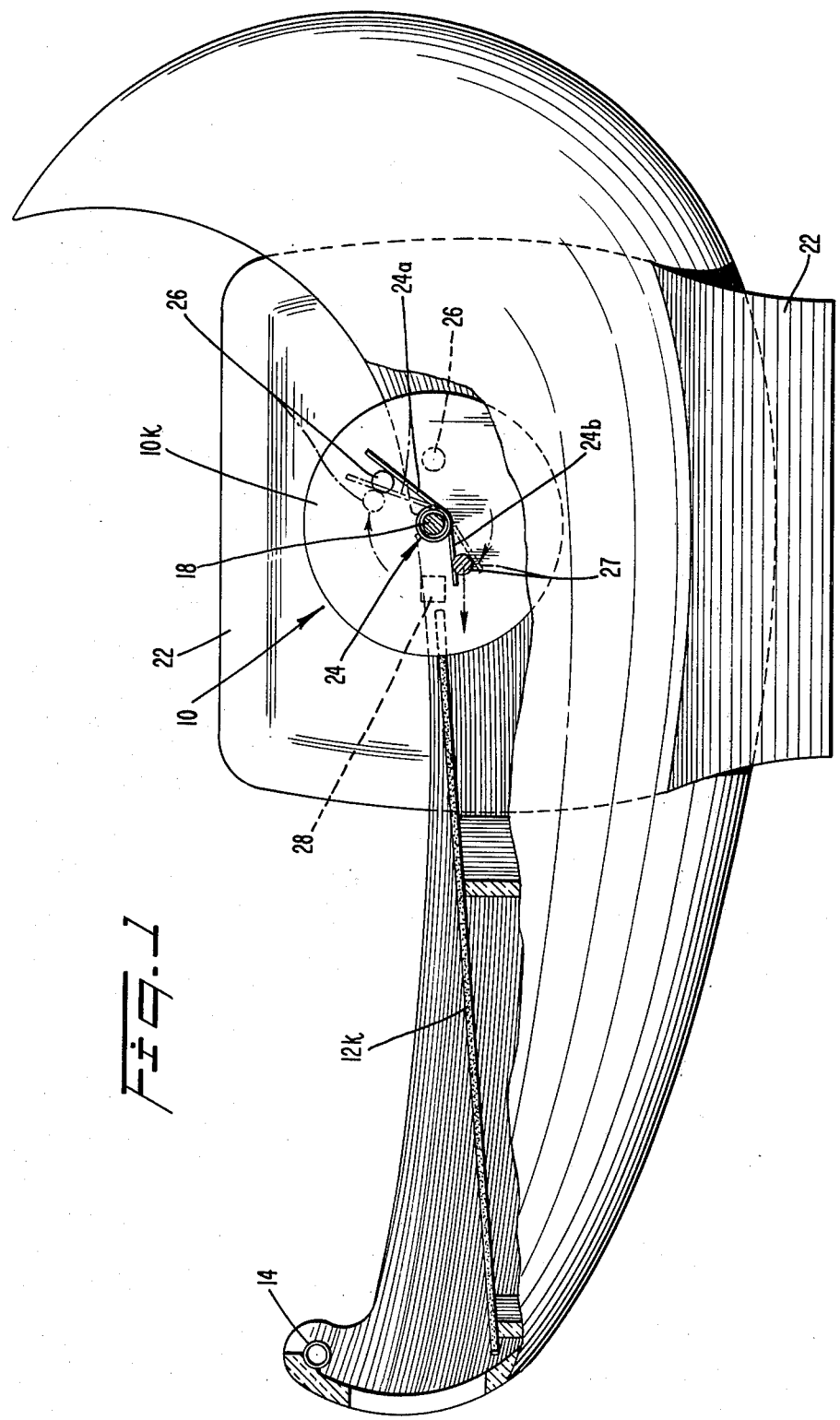
FIG. 1 is a side view of an incense burner apparatus constructed in accordance with the principles of the present invention.
Figure 2:
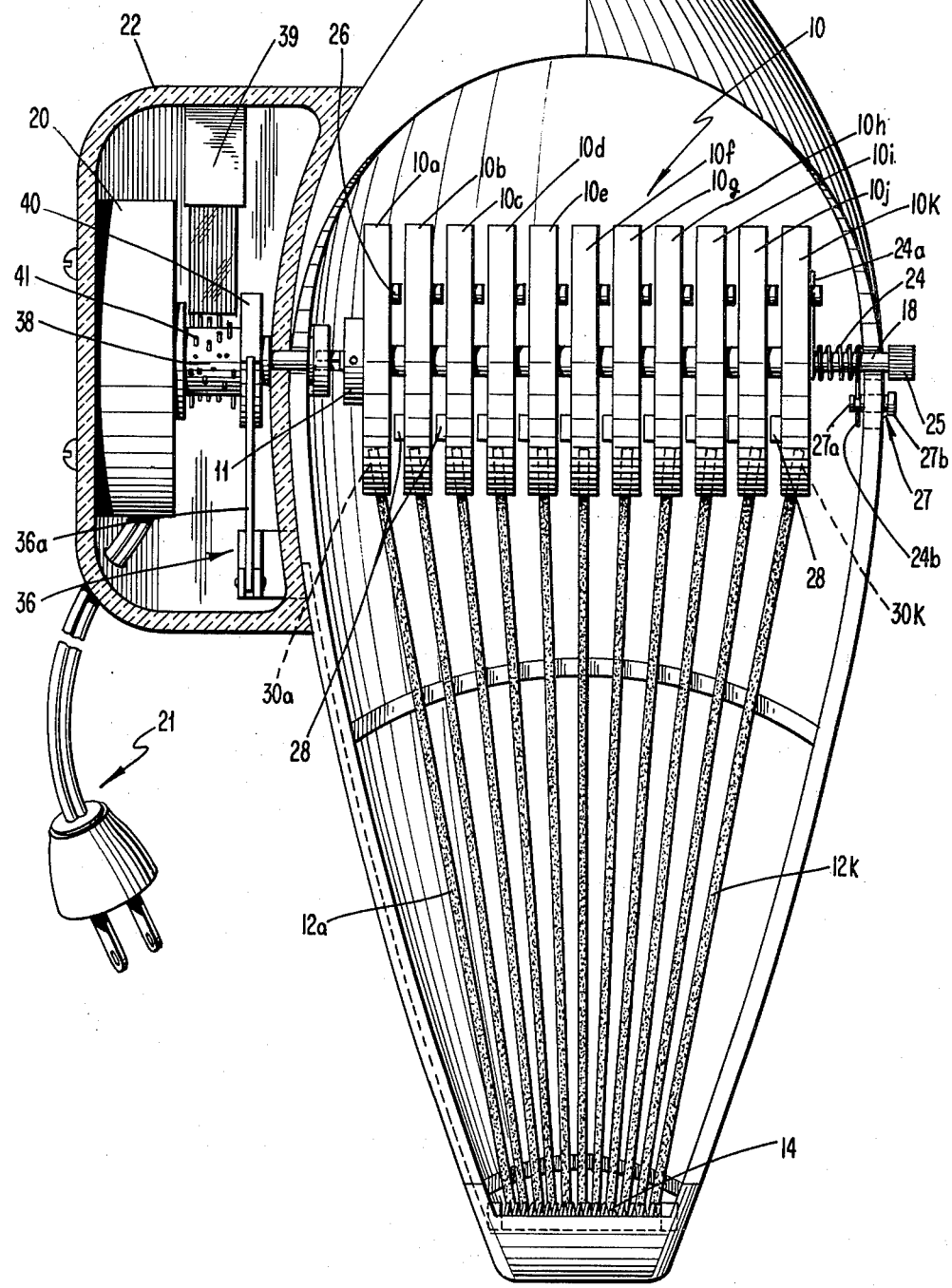
FIG. 2 is a cross-sectional top view of the apparatus illustrated in FIG. 1.

Referring to FIGS. 1-3, an apparatus for igniting and exposing to the atmosphere, one by one, a plurality of incense sticks 12a-12k or other elongated combustible articles, comprises an incense stick holder 10 for supporting and successively rotating incense sticks 12a-12k into contact with an igniter element 14. The holder 10 and igniter element 14 are supported within an ornamental housing 16, which by way of example, may be in the form of a gondola. Any other suitable form of housing 16 may, of course, be provided. The holder 10 (see FIG. 2) comprises a series of timer discs 10a-10k mounted on a common shaft 18 journaled to one side of the housing 16 and coupled to the output of an electric motor 20 mounted in motor compartment 22. The first or master timer disc 10a is secured to the common shaft 18 by a collar 11. The remaining timer discs 10b-10k, however, are journalled on the shaft 18 and are rotatable relative to the shaft. The discs 10a-10k are retained in the positions shown in FIG. 2 by a helical spring 24 located between end disc 10k and one wall of housing 16. A knob 25 extends outwardly from disc 10k through a bore formed in housing 16 to enable the discs 10 to be manually rotated.

The electric motor 20 is energized by household A.C. power through an on-off switch 27 mounted on housing 16. The switch 27 is indexed on or off by a slide switch operator having an inwardly extending portion 27a and an outwardly extending portion 27b. The portion 27b is manually operated by the user to turn the motor on; thereafter, the portion 27a is automatically operated to turn the motor off following an incense burning cycle, in a manner to be described in detail below.

Master disc 10a is formed with a tab 26 extending outwardly from one surface of the disc facing adjacent disc 10b. The corresponding surfaces of intermediate discs 10b–10k are also formed with tabs 26 whereas opposite surfaces of those discs are formed with additional tabs 28.

The rim of each of the timer discs 10a–10k is formed with a bore 30a–30k, respectively, for receiving one end of each of the incense sticks 12a–12k. The opposite end of each of the incense sticks 12a–12k is seated on a support member 32 beneath igniter element 14 within the housing 16. When the incense sticks 12a–12k are positioned within corresponding bores of the discs 10a–10k and on support 32, the discs are rotatably oriented in the position shown in FIG. 2 with tabs 26 and cooperating tabs 28 of adjacent discs displaced from each other by about 270 degrees.

Thus, during initial rotation of shaft 18 by motor 20, only the first or master disc 10a rotates with the shaft since the master disc and shaft are secured together at collar 11. The remaining discs 10b–10k are maintained stationary by the weight of incense sticks 12b–12k as the shaft 18 rotates. As the master disc 10a approaches 270 degrees of rotation, however, there is contact between tab 26 of master disc 10a and tab 28 of disc 10b. The disc 10b is thus caused to rotate with master disc 10a to rotate the second incense stick 12b of the series. When the second disc 10b has rotated about 270 degrees to cause tab 26 on the disc 10b to contact tab 28 on the next disc 10c of the series, the third disc 10c rotates to rotate the third incense stick 12c, and so on, until all of the incense sticks in the series have been rotated.

Igniter element 14 located on housing 16 above the incense sticks 12 when the sticks are supported on support 32 is electrically energized to self-heat and thereby ignite the ends of incense sticks 12a–12k as the sticks are successively rotated into contact with the lower surface portion of the element. Referring to FIG. 6, a source of electric energy 34, which is preferably conventional A.C. household line power obtained by plug 21 (see FIG. 2), is applied through the line switch 27 across the timer motor 20 as well as across igniter element 14 and normally open switch 36. A collar 38 having a cam surface 40 (see FIGS. 3, 4 and 5) that rotates with motor shaft 18 maintains the switch 36 normally open with the cam 40 in the position shown in FIG. 5. With line switch 27 normally closed to energize motor 20, the cam is rotated by the motor in the direction of the arrow. As the cam approaches the position shown in FIG. 4, the switch operator 36a is gradually lifted until the switch 36 is closed, energizing the igniter element 14. As the cam 40 continues to rotate to the position shown in FIG. 5, however, the switch operator 36a reopens switch 36, thereby de-energizing the igniter element 14. Thus, the igniter element 14 is energized throughout only a portion of the cycle of rotation of motor shaft 18. Igniter element 14 is accordingly energized only when an incense stick is in proximity to the element, as shown in the operating sequence of FIGS. 7–10.

Thus, referring to FIG. 7, as the first incense stick 12a is rotated into contact with igniter element 14, the switch 36 is closed, energizing the igniter to ignite the end of stick 12a. As the motor shaft 18 continues to rotate (see FIG. 8), the incense stick 12a also rotates for exposure of the burning incense material to the atmosphere and the switch 36 is operated by cam 40 to close, thereby de-energizing the igniter element 14. Referring to FIG. 9, as the shaft 18 further rotates, switch 36 is maintained closed while incense stick 12a becomes substantially consumed by burning. Finally, as shaft 18 continues to rotate, as shown in FIG. 10, a second incense stick 12b is rotated into contact with igniter element 14. Simultaneously, the switch 36 is controlled by cam 40 to close, thereby energizing the igniter 14 to ignite the end of the second incense stick.

The speed of rotation of motor 21 is determined as a function of burning duration such that an incense stick becomes substantially consumed during rotation of motor shaft 18 between the positions of FIGS. 7 and 10. As the shaft 14 rotates beyond the position shown in FIG. 10, the stub of the consumed incense stick will drop from bore 30 onto the bottom of housing 16 for subsequent disposal.

During rotation of the final disc 10k, spring leg 24a is contacted by the tab 26 of disc 10k (see position of leg 24a in phantom lines). As the disc 10k continues to rotate, spring 24 is rotated on shaft 18 until spring leg 24b contacts switch operator portion 27a and urges the switch 27 open, thereby denergizing motor 20 (see arrows in FIG. 1). The motor 20 remains de-energized until the line switch 27b is thereafter closed by manually sliding operator portion 27b.

The number of timer discs 10 provided on shaft 28 within housing 16 depends upon the number of incense sticks 12 to be burned. The number of discs 10 may be changed by adding or removing discs with respect to the shaft 18. The discs 10 may be released by removing the shaft 18 from between the housing wall and motor collar 38 after removing the external knob 25. Slack between discs 10 when the number of discs is decreased may be compensated by inserting a longer spring 24 on the shaft.

An array of pins 41 are formed on collar 38 of motor 20 to be plucked by the extending fingers of comb 39 as the collar rotates. The pins 41 are positioned on the collar 38 to cause a predetermined musical tune synchronized to rotation of the collar to be played during operation of holder 10. The collar 38 may be an overlay that is replaceable to play different musical tunes.

In this disclosure, there is shown and described only the preferred embodiments of the invention, but as aforementioned, it is to be understood that the invention is capable of use in various other combinations and environments and is capable of changes or modifications within the scope of the inventive concept as expressed herein.

For example, as an alarm, pins 41 may, if desired, be oriented on collar 38 to generate a sound each time an incense stick 12 has completed a burn cycle.

I claim:

1. An apparatus for successively igniting a plurality of incense sticks, comprising:
   an igniter member;
   means for supporting said plurality of incense sticks spaced apart from said igniter member;

means for rotating said incense sticks successively and sequentially into contact with said igniter member; and means for energizing said igniter member during contact with said incense sticks to sequentially ignite said sticks.

2. The apparatus of claim 1, wherein said rotating means includes means for further rotating said ignited incense sticks for exposure to the atmosphere.

3. The apparatus of claim 1, wherein said rotating means includes timer means for initiating rotation of said incense sticks at predetermined times corresponding to a burning duration of said sticks.

4. The apparatus of claim 1, wherein said igniter member includes an electrical heating element and switch means in circuit between said heating element and a source of electrical energy and synchronizing means for closing said switch means to energize said heating element each time one of said incense sticks is in proximity to said heating element.

5. The apparatus of claim 1, wherein said rotating means includes an electric motor, manual means for connecting said electric motor to an electric source and means for disconnecting said electric motor from said source in response to completion of a burning cycle.

6. The apparatus of claim 1, including means synchronized to said rotating means for generating musical sounds.

7. The apparatus of claim 1, wherein said rotating means includes a plurality of rotary elements positioned coaxially on a common shaft, each of said rotary elements including gripping means for gripping an end of one of said incense sticks, means for coupling together adjacent ones of said rotary elements, and means for imparting rotation to one of said rotary elements.

8. The apparatus of claim 7, wherein said igniter member includes cam means positioned on said shaft adjacent said switch means for operating said switch means, said cam means having a profile to close said switch means each time one of said incense sticks is in contact with said heating element.

9. The apparatus of claim 7, including an end support for supporting and retaining together ends of said plurality of incense sticks, the opposite ends of said incense sticks being gripped by said gripping means of said rotary elements.

10. The apparatus of claim 7, wherein said rotary elements are disc-shaped.

11. The apparatus of claim 7, wherein said rotating means includes an electric motor, manual means for connecting said electric motor to an electric source and means for disconnecting said electric motor from said source in response to completion of a burning cycle.

12. The apparatus of claim 11, wherein said disconnecting means includes an electric switch and spring means extending between said rotary elements and said switch, said spring means being urged by said rotary elements to close said switch at the end of an incense burning cycle.

13. An apparatus for successively igniting a plurality of combustible articles, comprising:

an igniter member;

means for storing a plurality of said combustible articles;

means for sequentially moving said combustible articles from said storing means, one at a time, to said igniter member; and means for energizing said igniter member when each of said combustible articles is in proximity to said igniter member to be ignited thereby.

14. The apparatus of claim 13, wherein said igniter member is an electrical resistance element and said energizing means includes means for electrically energizing said element when each of said combustible articles are in contact with said element.

15. The apparatus of claim 13, wherein said moving means includes means for rotating said combustible articles, one by one, from said storing means to said igniter member for ignition and thereafter further rotating said combustible articles for exposure to the atmosphere.

16. The apparatus of claim 15, wherein said rotating means includes a series of intercoupled disc members, and said gripping means includes a bore formed in a rim of each of said disc members to receive an end of one of said combustible articles.

17. The apparatus of claim 16, wherein said energizing means includes switch means connected between a power source and said igniter member and means synchronized to said rotary means for repetitively operating said switch means.

* * * * *